(12) United States Patent
Carrillo

(10) Patent No.: US 12,245,769 B2
(45) Date of Patent: Mar. 11, 2025

(54) ANEURYSM TREATMENT DEVICE AND ASSOCIATED SYSTEMS AND METHODS OF USE

(71) Applicant: Covidien LP, Mansfield, MA (US)

(72) Inventor: Ramon Carrillo, Santa Ana, CA (US)

(73) Assignee: COVIDIEN LP, Mansfield, MA (US)

( * ) Notice: Subject to any disclaimer, the term of this patent is extended or adjusted under 35 U.S.C. 154(b) by 207 days.

(21) Appl. No.: 18/053,181

(22) Filed: Nov. 7, 2022

(65) Prior Publication Data
US 2023/0157696 A1 May 25, 2023

Related U.S. Application Data

(60) Provisional application No. 63/263,751, filed on Nov. 8, 2021.

(51) Int. Cl.
*A61B 17/12* (2006.01)
*A61B 17/00* (2006.01)

(52) U.S. Cl.
CPC .. *A61B 17/12113* (2013.01); *A61B 17/12172* (2013.01); *A61B 2017/00867* (2013.01)

(58) Field of Classification Search
CPC ........ A61B 17/12113; A61B 17/12172; A61B 2017/00867
See application file for complete search history.

*Primary Examiner* — Ryan J. Severson
(74) *Attorney, Agent, or Firm* — Fortem IP LLP

(57) ABSTRACT

An aneurysm treatment device includes a tip portion, a body portion, and a base portion. The device is configured to radially self-expand within an aneurysm, with the tip portion engaging a dome portion of the aneurysm, the body portion filling most of the aneurysm volume, and the base portion extending across the aneurysm neck to prevent migration of the device.

17 Claims, 8 Drawing Sheets

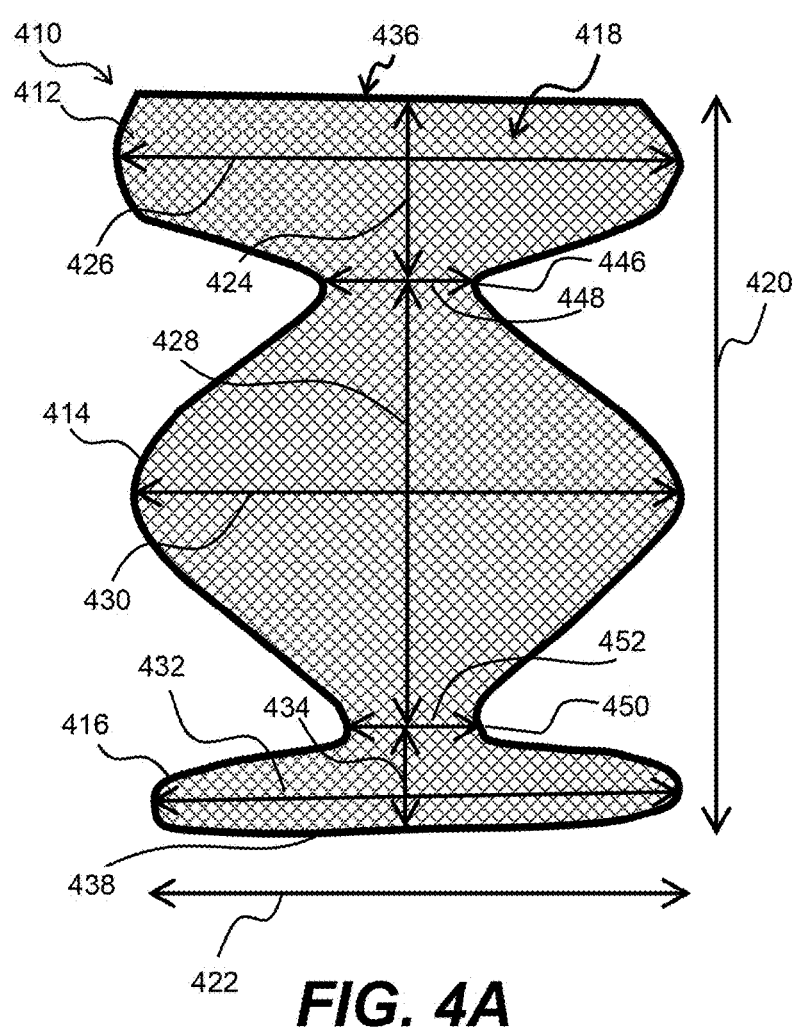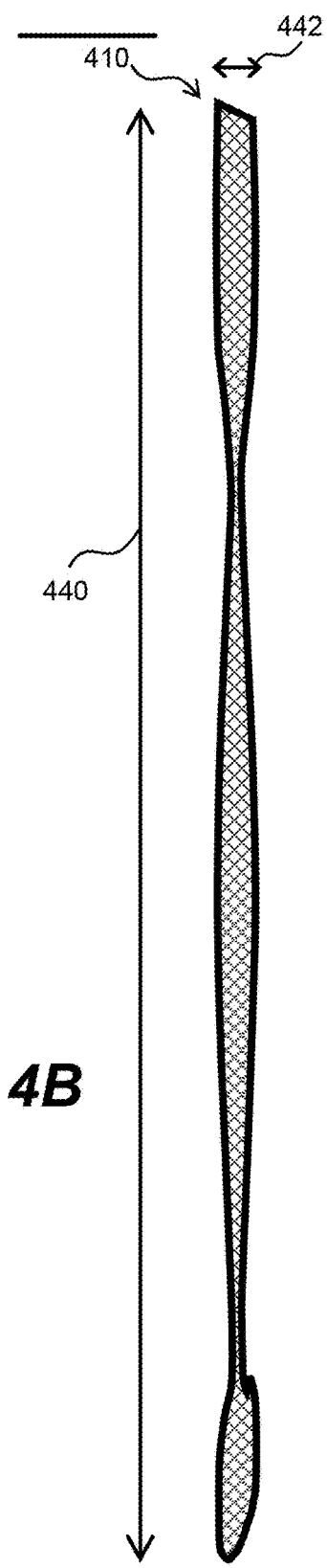
FIG. 4A
FIG. 4B

ANEURYSM TREATMENT DEVICE AND ASSOCIATED SYSTEMS AND METHODS OF USE

CROSS-REFERENCE TO RELATED APPLICATION(S)

The present application claims the benefit of priority to U.S. Provisional Patent Application No. 63/263,751, filed Nov. 8, 2021, which is incorporated by reference herein in its entirety.

TECHNICAL FIELD

The present technology relates to implantable devices for treating vascular defects and associated systems and methods of use. In particular, the present technology is directed to an endoluminal therapeutic device for treating aneurysms.

BACKGROUND

Aneurysms are blood-filled dilations of a blood vessel generally caused by disease or weakening of the blood vessel wall. The wall of the aneurysm may progressively thin, which increases the risk of rupture causing hemorrhagic stroke or even sudden death. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures. There are about 30,000 to 40,000 cases of aneurysmal rupture per year in the United States, accounting for about 5% of all strokes. The prognosis after aneurysmal rupture is poor; the 30-day mortality rate is approximately 45% and a positive functional outcome is achieved in only 40-50% of survivors.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Numerous companies have pursued ball-type embolization devices for aneurysm treatment. Generally, ball-type embolic devices for aneurysm treatment and/or other types of embolization operate through blood flow disruption and subsequent thrombus formation.

SUMMARY

Systems and procedures for treating aneurysms can include an embolization device having one or more expandable components that can be inserted into an aneurysm to facilitate a thrombotic, healing effect. The components can have distinct and specific characteristics, including porosity, composition, material, shape, size, coating, and the like. These characteristics can be selected in order to achieve a desired treatment or placement of the device.

In accordance with some embodiments, the device can comprise at least three portions formed of a single, continuous mesh. The mesh can be shape set such that each of the portions comprise different shapes and/or sizes. One portion of the mesh can be configured as a neck cover that prevents the device from migrating or otherwise advancing out of the aneurysm via the aneurysm neck. Another portion of the mesh can be configured as an atraumatic tip portion that can be placed into an aneurysm first to provide subsequently-delivered portions a cushion when received within the aneurysm. Yet another portion may comprise a volume-filling member which expands to fill the majority of the volume of the aneurysm. Accordingly, the implantable meshes of the present technology advantageously integrate multiple functionalities into a single device.

The present technology is illustrated, for example, according to various aspects described below. Several aspects of the technology comprise an aneurysm embolization device configured to be self-expandable from a compressed state to an expanded configuration. The device comprises a body portion having a first end, a second end, and a side extending between the first and second ends. The body portion is self-expandable to an expanded configuration. The body portion is configured to be positioned in an intracranial aneurysm in the expanded configuration such that at least a portion of the outer surface engages the aneurysm wall. The device further comprises an atraumatic tip portion extending from the first end of the body portion. The tip portion is self-expandable to an expanded configuration having a different shape and/or size than the expanded configuration of the body portion. The atraumatic tip portion is configured to be positioned against a dome portion of an aneurysm wall in the expanded configuration. The device can further include a base portion extending from the second end of the body portion and being self-expandable to an expanded configuration that is different in shape and/or size than the expanded configuration of the body portion. The base portion comprises a neck-engaging surface and is configured to be positioned at a neck of an intracranial aneurysm in its expanded configuration such that base portion extends across the neck and the neck-engaging surface engages against a neck portion of the aneurysm wall surrounding the neck.

Several aspects of the technology include an aneurysm embolization device comprising a memory shape-set configuration. The device is configured to be compressed to a delivery configuration and is configured to self-expand from the delivery configuration toward the memory shape-set configuration. The device further comprises a body portion, an atraumatic tip portion, and a base portion. The body portion has a body portion distal end, a body proximal distal end, and a body portion outer surface extending between the body portion distal end and the body proximal distal end. With the device in the memory shape-set configuration, the body portion comprises a body portion pre-set configuration. The body portion is configured to be positioned in an intracranial aneurysm such that at least some portions of the body portion outer surface engage against the aneurysm wall. The atraumatic tip portion extends from the body portion distal end and, with the device in the memory shape-set configuration, comprises a tip portion pre-set configuration that is different in shape and/or size from the body portion pre-set configuration. The tip portion comprises a tip portion distal surface and a tip portion proximal surface, wherein the tip portion distal surface is configured to engage against a dome portion of the aneurysm wall. The base portion extends from the proximal end of the body portion and, with the device in the memory shape-set configuration, comprises a base portion pre-set configuration that is different in shape and/or size from the body portion pre-set configuration. The base portion comprises a base portion distal surface and a base portion proximal surface. At least a portion of the base portion proximal surface is configured to engage against a neck portion of the aneurysm wall surrounding a neck of the aneurysm.

Aspects of the technology can include a method of treating an aneurysm in a patient's body. The method comprises advancing a distal portion of a delivery catheter through a patient's vasculature to an aneurysm where the distal portion releasably holds an aneurysm treatment device in a radially compressed configuration. The aneurysm treatment device comprises a tip portion, a body portion, and a base portion. The tip portion is secured to the body portion at a distal waist, and the base portion is secured to the body portion at a proximal waist. The method further comprises releasing the aneurysm treatment device from the distal portion of the delivery catheter to radially expand inside the aneurysm and engage against wall portions of the aneurysm.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 4A and 4B are side cross-sectional views of a device in accordance with some embodiments in pre-set and delivery configurations, respectively.

DETAILED DESCRIPTION

Figure 1A:
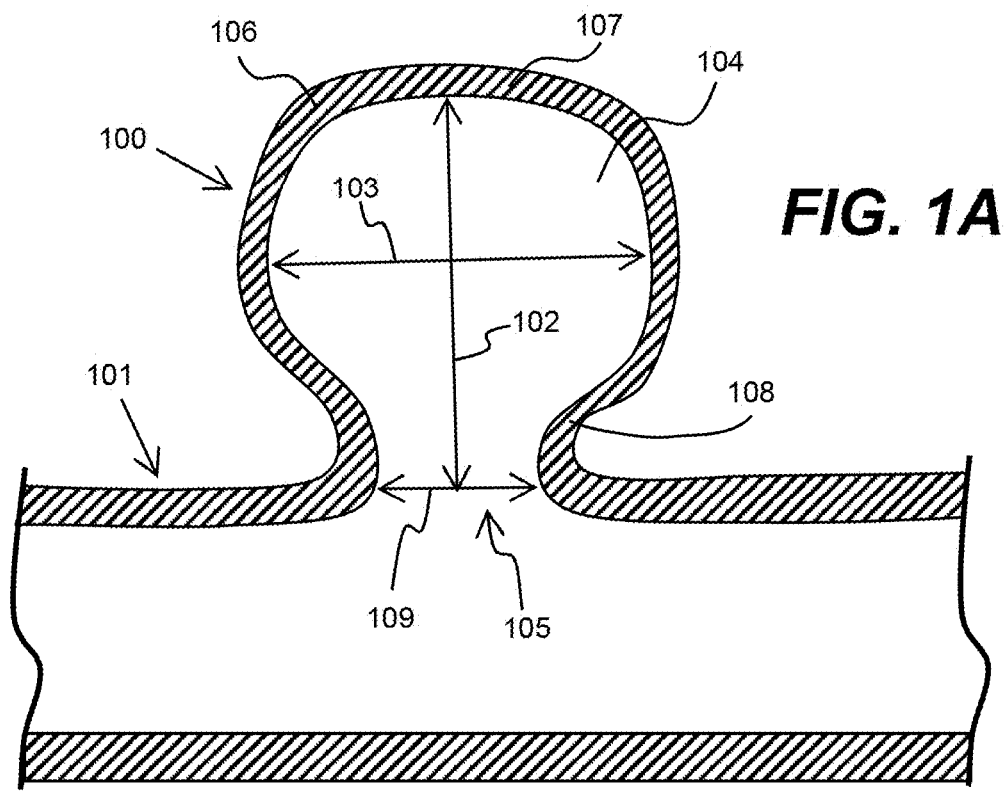
FIG. 1A is a side cross-sectional illustration of an aneurysm for treatment with a device configured in accordance with some embodiments.

Specific details of several embodiments of the present technology are described herein with reference to FIGS. 1A-7B. Although many of the embodiments are described with respect to devices, systems, and methods for embolization of aneurysms, other applications and other embodiments in addition to those described herein are within the scope of the present technology, and can be employed in any of the embodiments of systems disclosed herein. It should be noted that other embodiments in addition to those disclosed herein are within the scope of the present technology. Further, embodiments of the present technology can have different configurations, components, and/or procedures than those shown or described herein. Moreover, embodiments of the present technology can have configurations, components, and/or procedures in addition to those shown or described herein and that these and other embodiments may not have several of the configurations, components, and/or procedures shown or described herein without deviating from the present technology.

As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device. The headings provided herein are for convenience only and should not be construed as limiting the subject matter disclosed.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments may be disclosed or shown in the context of aneurysm therapy, such embodiments can be used in other applications. Furthermore, various applications of such embodiments and modifications thereto, which may occur to those who are skilled in the art, are also encompassed by the general concepts described herein.

Delivery systems, implants, and methods of making the implants are provided herein. The implant can be useful for treating neurovascular defects, such as in intracranial aneurysm embolization/occlusion.

In accordance with some embodiments disclosed herein, an embolization implant or device can comprise two or more portions, or three or more portions, with each portion having different shapes or configurations, which can enable the device to provide distinct functions or operational characteristics. The device can comprise a single, continuous piece of material that extends along each of the portions thereof.

The piece of material can be shape set such that each of the portions achieves a desired shape or configuration. Accordingly, because some embodiments of the device use only a single piece of material, the device can advantageously integrate various functions previously performed by several devices into a continuous device. Thus, some embodiments allow the device to perform various discrete functions while operating as a unitary or single component.

For example, some embodiments of the implant can be formed from tubular braid stock comprising a resilient material that defines an hour-glass shape in an uncompressed/unconstrained state. The device can be deployed within an aneurysm sac. The implant can be delivered by access through the trunk vessel (e.g., the basilar artery), such as through a commercially available microcatheter with a delivery system, such as that described herein.

The device can comprise at least three portions: a tip portion comprising an atraumatic tip or framing portion, a body portion comprising a volume-filling portion, and a base portion comprising a neck blocking portion. In some embodiments, the tip portion can be configured to precede the base portion when being placed into an aneurysm. In such embodiments, the tip portion can be shape set to prevent injury and/or perforation of the aneurysm wall during delivery of the device. For example, the tip portion can be curved and/or softer (relative to the rest of the device). Further, the body portion can be shape set to expand into one or more expandable components that can be advanced into an aneurysm to fill or pack the aneurysm cavity. The base portion can be shape set to block the neck or ostium of the aneurysm to prevent herniation of embolic material therefrom. However, the order of placement can also be reversed or otherwise reordered. For example, in some embodiments the base portion can be advanced first into the aneurysm, or the body portion can be advanced first into the aneurysm.

In some embodiments, the device can have a predetermined configuration, whether or not the device has only a single or multiple expandable components. The predetermined configuration can be based on typical aneurysm shapes, thereby allowing selection of a specific device. However, individual components of a device can also be arranged based on desired properties.

In some embodiments, expandable component(s) of the first and/or second and/or third portions of the device may be shape set or manufactured into a variety of geometrical or partial geometrical shapes.

Aneurysms can be in various shapes and sizes. For example, a cerebral aneurysm may present itself in the shape of a berry, i.e., a so-called berry or saccular aneurysm, which is a bulge in the neurovascular vessel. Berry aneurysms may be located at bifurcations or other branched vessels. Other types of aneurysms, including fusiform aneurysms, can also be treated using embodiments of the devices disclosed herein.

For example, in order to accommodate a variety of aneurysm configurations, the shape or size of the expandable component(s) can be selected from a variety of spherical or non-spherical shapes, including, cylinders, hemispheres, noodles, polyhedrons (e.g., cuboids (types), tetrahedrons (e.g. pyramids), octahedrons, prisms), coils, prolate spheroids, oblate spheroids, plates (e.g., discs, polygonal plates), bowls (e.g., an open container, such as a hollow, hemispherical container or other open, hollow containers, whether hemispherical, rounded, or otherwise), non-spherical surfaces of revolution (e.g., toruses, cones, cylinders, or other shapes rotated about a center point or a coplanar axis), and combinations thereof.

A variety of delivery systems and procedures can be implemented to deliver a device having a specific size or shape and, in some embodiments, having a plurality of expandable components. Further, systems and methods are provided for delivery of a device to an aneurysm and/or recapturing the device for removal or repositioning. Examples of these systems and procedures are discussed further herein.

Additionally, although in some embodiments, a single device can be used alone to fill the aneurysm and provide a desired packing density or fill volume, a plurality of devices can also be used to fill the aneurysm and provide a desired packing density or fill volume.

Optionally, a liquid embolic and/or a framing component can be used in combination with one or more devices to facilitate delivery, engagement with the aneurysm, or increase of the packing density or fill volume. Any of these embodiments can allow increased packing density or fill volume to avoid recanalization of the aneurysm.

Referring now to the drawings, FIG. 1A illustrates an aneurysm 100 in a blood vessel 101. The aneurysm 100 depicted comprises a maximum width 103, a maximum height 102, a volume 104, and a neck 105. The aneurysm 100 has an aneurysm wall 106 which includes a dome portion 107 and a neck portion 108, with the neck portion 108 adjacent to and surrounding the neck 105. The neck 105 has a maximum dimension 109 (e.g., maximum diameter or width).

Figure 1B:
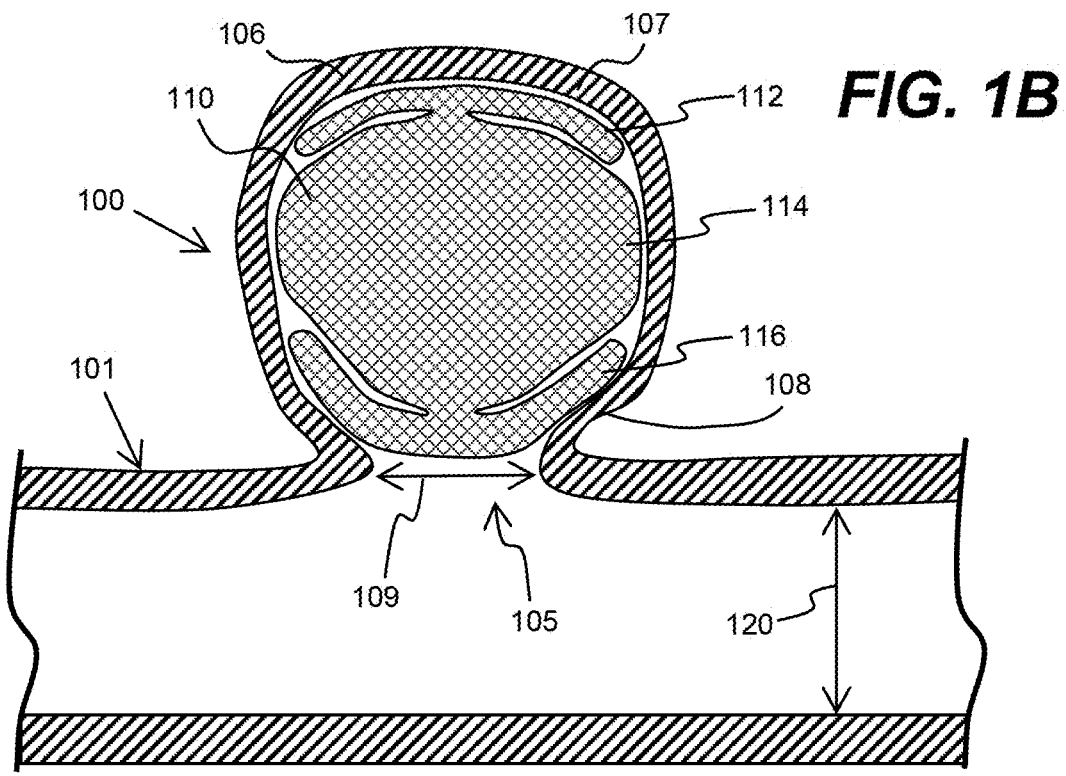
FIG. 1B is a side cross-sectional illustration of an aneurysm with a device deployed therein in accordance with some embodiments.

FIG. 1B depicts an embolization device 110 deployed within the aneurysm 100. In the embodiment depicted, the device 110 comprises a plurality of expandable components, namely a tip portion 112, a body portion 114, and a base portion 116. The device 110 is depicted in an expanded/deployed configuration. As shown, The body portion 114 fills most of the volume of the aneurysm 100. The body portion 114 as depicted may be substantially spherical in shape when expanded within the aneurysm 100, and/or may substantially conform to the shape of the aneurysm 100. Portions of the body portion 114 may engage against portions of the aneurysm wall 106. The expanded deployed shape of the body portion 114 may be a pre-set shape, such as a substantially spherical shape. The expanded deployed shape of the body portion 114 be different from the pre-set shape, such as where the body portion 114 is deformed from the pre-set shape as a result of pressure from the aneurysm wall 106 pressing inwardly against the body portion 114. The body portion 114 is thus restricted from achieving its full pre-set shape because of the inward pressure from the aneurysm wall 106.

The tip portion 112 may be interposed between the body portion 114 and the dome portion 107 of the aneurysm wall 106, with the tip portion 112 engaging against the dome portion 107. The tip portion 112 may be configured as an atraumatic tip to prevent injury and/or rupture of the already-weakened aneurysm wall. The expanded deployed shape of the tip portion 112 may substantially conform to the curve of the dome portion 107. The expanded deployed shape of the tip portion 112 may be a pre-set shape, such as a substantially curved disk-like shape. The expanded deployed shape of the tip portion 112 be different from the pre-set shape, such as where the tip portion 112 is deformed from the pre-set shape as a result of pressure from the dome portion 107 of the aneurysm wall 106 pressing inwardly against the tip portion 112. The tip portion 112 is thus restricted from achieving its full pre-set shape because of the pressure from the dome portion 107.

The base portion 116 may have sufficient width to extend entirely across the neck 105, and to engage against the neck portion 108 surrounding the neck 105. With the device 110 deployed in the aneurysm 100, the base portion 116 may be interposed between the body portion 112 and the neck 105 of the aneurysm 100. The base portion 116 may serve to prevent the device 110 from migrating out of the neck 105 and into the blood vessel 101, and also serves as an additional flow-disrupting layer (in addition to the flow-disruption portions of the body portion 114 and tip portion 112). The expanded deployed shape of the base portion 116 may substantially conform to the curve of the neck portion 108. The expanded deployed shape of the base portion 116 may be a pre-set shape, such as a substantially curved disk-like shape. The expanded deployed shape of the base portion 116 be different from the pre-set shape, such as where the base portion 116 is deformed from the pre-set shape as a result of pressure from the neck portion 108 of the aneurysm wall 106 pressing against the base portion 116. The tip portion 116 is thus restricted from achieving its full pre-set shape because of the pressure from the neck portion 108. Note that the portion of the base portion 116 which bridges across the neck 105 in the expanded deployed shape may preferably have sufficient stiffness to hold the rest of the device (e.g., the tip portion 112 and the body portion 114) within the aneurysm 100, thereby preventing the device 110 from migrating out of the aneurysm 100 and into the blood vessel 101.

The device 110 may be formed as a single, unitary structure. For example, the body portion 112 and the tip portion 114 and the base portion 116 may comprise a single, continuous braid, a plurality of braided filaments, a knitted material, or a woven material. Further, in some embodiments, the device 110 can comprise a tubular mesh that is shape set to define the tip, body, and base third portions 112, 114, 116. For example, with regard to the body portion 114, a tubular mesh or other formation thereof can be shape set such that the body portion 114 defines an open volume and the filaments converge toward proximal and distal ends of the body portion to form a generally ellipsoidal shape. The device 110 may be formed from various bio-compatible materials, such as metals or polymers. The device 110 may be formed from memory materials, such as Nitinol, and may be self-expanding when released from a compressed form. The device 110 may comprise a mesh-like or other flow-disrupting structure which disrupts fluid flow therethrough, e.g., allowing only small amounts of blood and/or slow-speed blood flow therethrough, but preventing large amounts of blood flow, and/or high-speed blood flow, therethrough. Such flow-disrupting construction can encourage embolization of the aneurysm.

Note that a given expandable component of the device 110 can have one or more different characteristics than another of the expandable components of the device 110. One or more (or all) of the expandable components can be formed from a material that can be highly compressed.

Figure 2A:
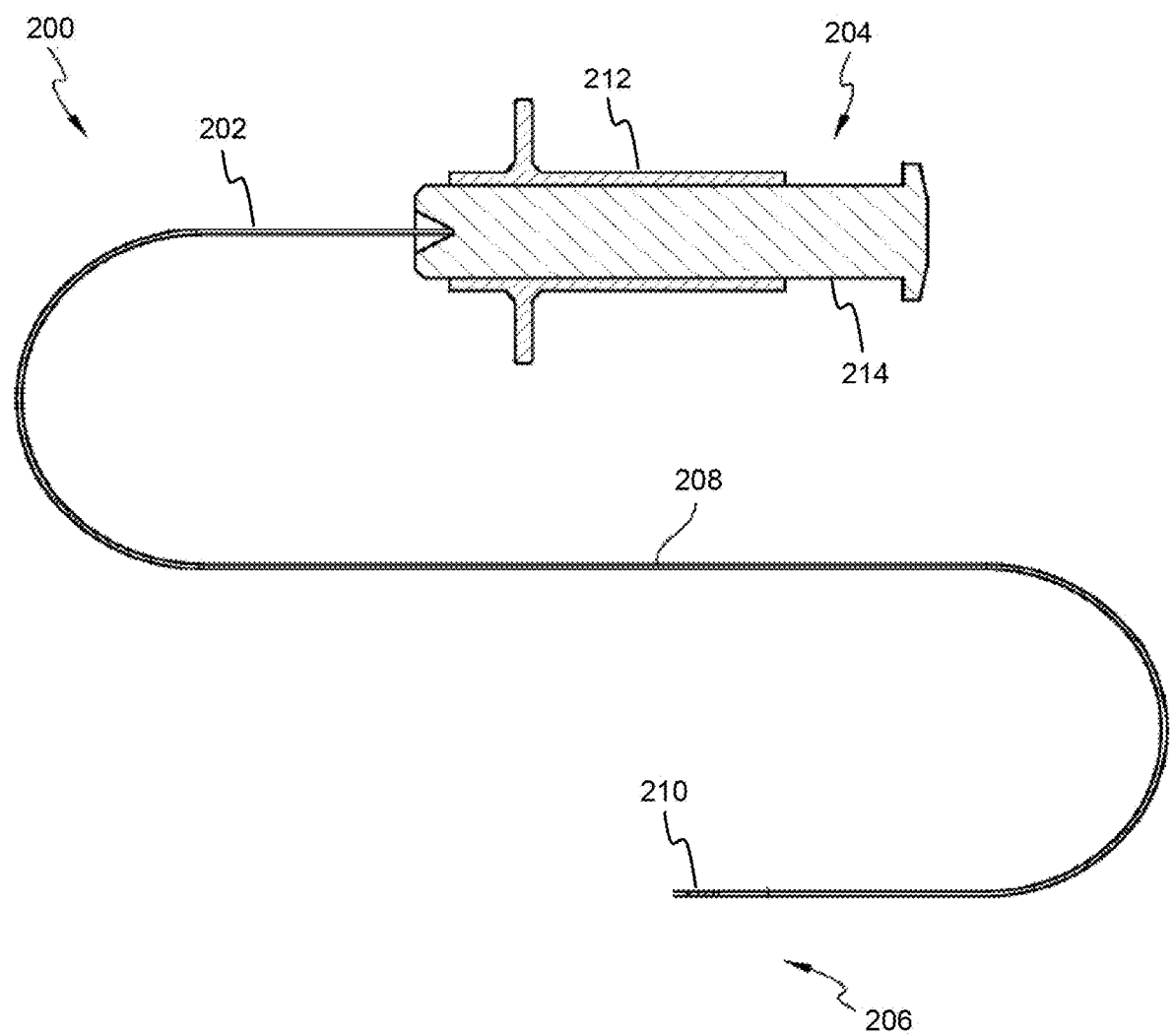
FIG. 2A is a side cross-sectional view of a medical device delivery system in accordance with some embodiments.

FIG. 2A depicts a system 200 for treating an aneurysm. The system 200 may include a delivery catheter 202 (e.g., delivery tube or microcatheter) having a proximal portion 204 and a distal portion 206, with an elongated catheter body 208 extending therebetween. An embolization device 210 is positioned in the distal portion 206 in a compressed/delivery configuration. A handle 212 may have controls 214 which a user can activate to release and retract the embolization device 210.

Figure 2B:
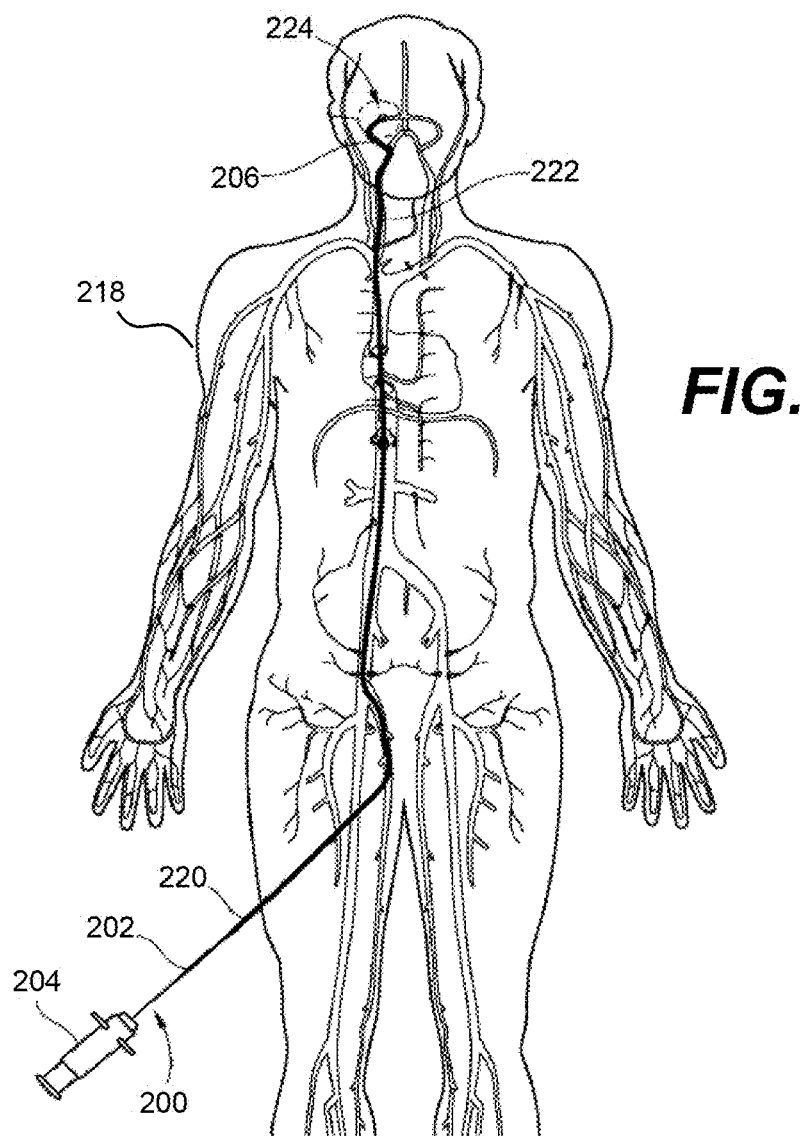
FIG. 2B is a plan view of a medical device delivery system within a human body.

FIG. 2B shows the system 200 of FIG. 2A advanced inside vasculature of a patient 218. In the embodiment shown in FIG. 2B, an operator uses a guide tube or guide catheter 220 to position a delivery catheter 202 (e.g., delivery tube or microcatheter) in a patient's vasculature. This procedure involves inserting the guide catheter 220 into the patient's vasculature through an access point such as the groin, and directing the distal end 222 of the guide catheter 220 through the vascular system until it reaches the carotid artery. After removing a guide wire (not shown) from the guide catheter 220, a delivery catheter 202 may be inserted into and advanced through the guide catheter 220 until the distal portion 206 of the delivery catheter 202 subsequently exits the guide catheter distal end 222. The distal portion 206 may be advanced through the vasculature to be positioned near the target site 224, such as an aneurysm in the patient's brain.

Figure 2C:
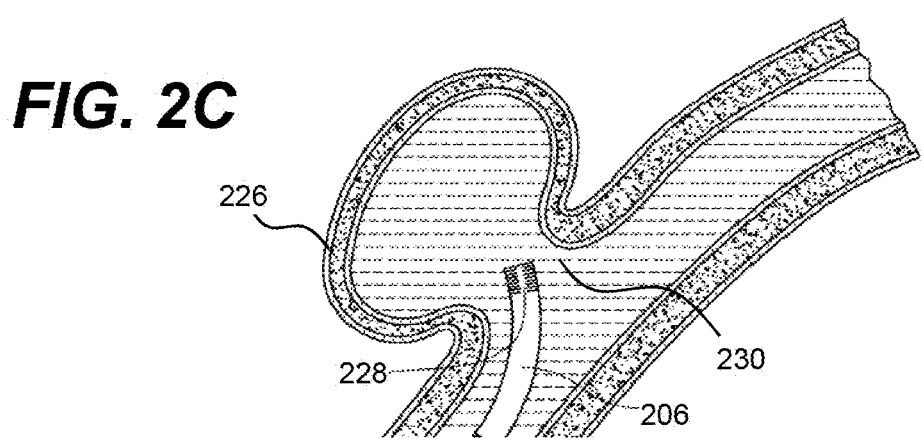
FIG. 2C is a side cross-sectional view of a medical device delivery system advanced to an aneurysm in accordance with some embodiments.

FIG. 2C depicts the delivery catheter distal portion 206 positioned at an aneurysm 226 for treatment. The catheter distal portion 206 is positioned with the distal end 222 advanced into the neck 230 of the aneurysm 226.

Figure 3A:
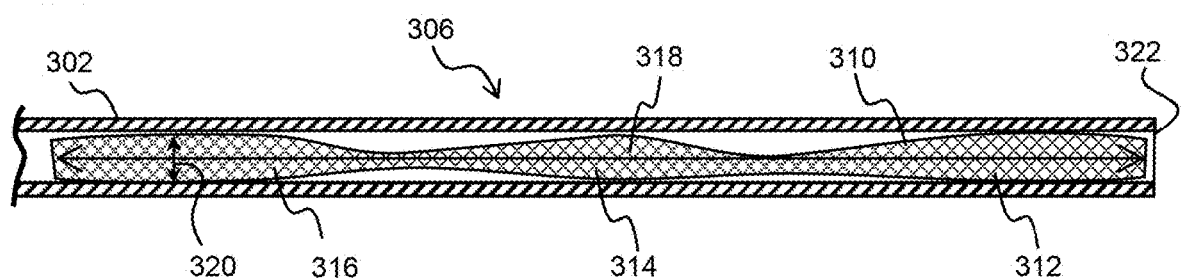
FIGS. 3A-3D are side cross-sectional views of a device being deployed from a delivery catheter in accordance with some embodiments.
Figure 3B:
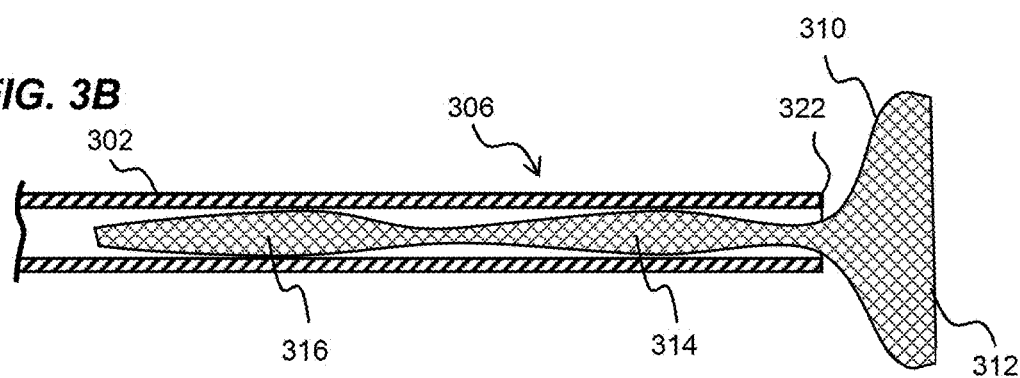
Figure 3C:
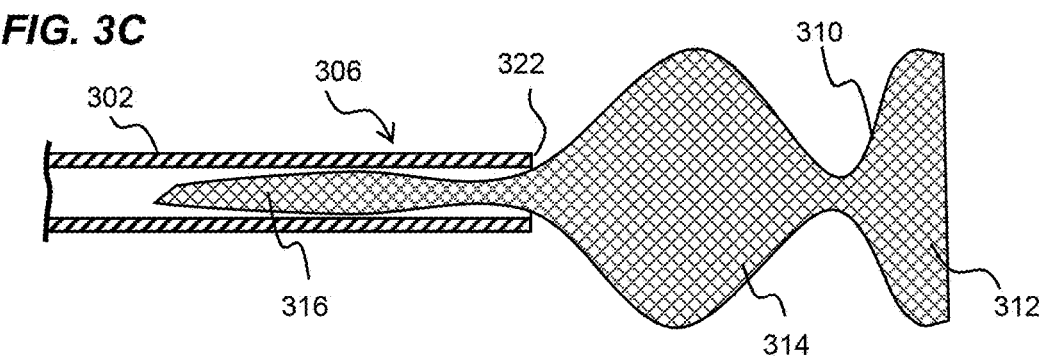
Figure 3D:
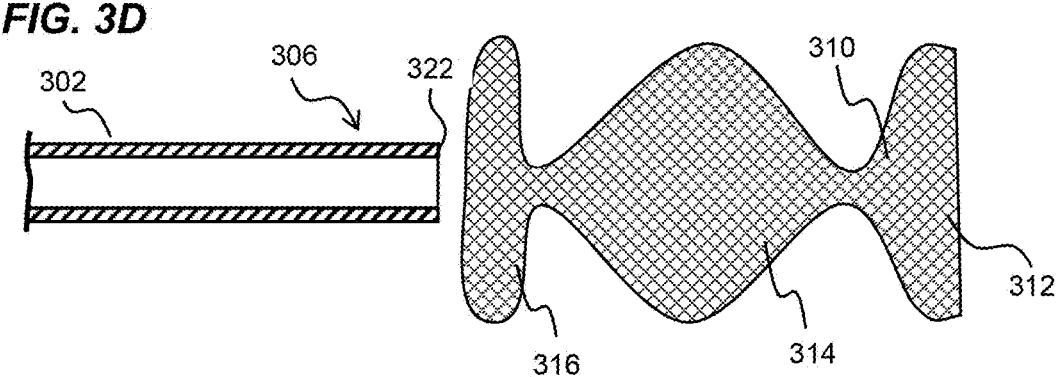

Deployment of a device 310 from a catheter 302 is depicted in FIGS. 3A-3D. As shown in FIG. 3A, during delivery (including advancement of the catheter 302 through the patient's vasculature) the device 310 may be held at or in the catheter distal portion 306 in a compressed delivery configuration, where the device 310 has an overall length 318 and a maximum diameter 320. With the catheter distal end 322 positioned at a desired location, the tip portion 312 of the device 310 is released to radially expand, such as by being advanced out of the catheter distal end 322 (such as by pushing the device 310 out of the catheter distal end 322 and/or retracting the catheter distal portion 306 from around the device 310) as depicted in FIG. 3B. The body portion 314 is then released to radially expand, such as by being advanced out of the catheter distal end 308 advanced out of the catheter distal end 322 (such as by pushing the device 310 out of the catheter distal end 322 and/or retracting the catheter distal portion 306 from around the device 310) as depicted in FIG. 3C. The base portion 316 is then released to radially expand, such as by being advanced out of the catheter distal end 322 (such as by pushing the device 310 out of the catheter distal end 322 and/or retracting the catheter distal portion 306 from around the device 310), at which point the device 310 is fully expanded as depicted in FIG. 3D.

FIGS. 3A-3D depict the device 310 expanding to its pre-set shape. Where the device 310 has a pre-set configuration (e.g., using memory material such as Nitinol), the device 310 as deployed may have dimensions (e.g., overall length and diameter, portion lengths and diameters, etc.) which may differ from the pre-set configuration dimensions. When deployed in an aneurysm, the device 310 will be biased to its pre-set shape, but the engagement between the device and the aneurysm will cause the device to distort to a different shape which may fill most of the aneurysm volume and may roughly correspond to the aneurysm pre-treatment shape. Such a deployed shape within the aneurysm will typically be shorter in length than the pre-set shape, and/or may include the device body portion being somewhat wider than in the pre-set shape. The variation in dimensions between pre-set and actual expanded/deployed dimensions is a result of interaction of the device with the aneurysm walls, which will reshape the device. This ability of the device to reshape responsive to interaction with the aneurysm wall helps the device to properly fill and embolize the aneurysm. Such deployed shapes are depicted in FIGS. 5A-5C and 6A-6C, and discussed below.

Note that after the base portion 316 is released to expand, the device 310 may still be held to the catheter 302, such as via a grasping element and/or stem and/or wire and/or other structure(s) (not shown). This can permit the expanded device 310 to be repositioned (such as by pulling or pushing on the device 310), and/or retracted fully or partially into the catheter distal end 308 for withdrawal and/or repositioning.

Details of a device 410 according to some embodiments are depicted in FIGS. 4A-4B. FIG. 4A depicted a side view of a device 410 in a pre-set configuration, with the device 410 having a tip portion 412, body portion 414, and base portion 416. A device lumen 418 extends lengthwise through the device 410, with the device lumen 418 varying in inner diameter along the length of the device 410. The device 410 may be open at its distal end 436 and/or its proximal end 438. The proximal end 438 may preferably not be open (other than the regular openings in the mesh-like material of the device), in order to maximize flow disruption in and out of the aneurysm.

The device 410 has an overall length 420 and maximum width 422. The tip portion 412 has a tip portion length 424 and tip portion maximum diameter 426. The body portion 414 has a body portion length 428 and body portion maximum diameter 430. The base portion 416 has a base portion length 434 and base portion maximum diameter 432. Note that the pre-set configuration may be pre-set using memory materials such as Nitinol, and is biased toward that pre-set configuration. When the device is released from constraints (e.g., compressive or expansive), the device will return toward the pre-set configuration.

The tip portion 412 meets the body portion 414 at a distal waist 446, which has a distal waist diameter 448. The base portion 416 meets the body portion 414 at a proximal waist 450, which has a distal waist diameter 452. The distal waist diameter 448 may be less than the tip portion maximum diameter 426 and/or less than the body portion maximum diameter 430 and/or less than the base portion maximum diameter 434. The proximal waist diameter 452 may be less than the tip portion maximum diameter 426 and/or less than the body portion maximum diameter 430 and/or less than the base portion maximum diameter 434. The distal waist diameter 448 and/or the proximal waist diameter 452 may be narrower than any other portions of the device 410.

The body portion 414 may preferably have a pre-set body portion length 428 which is substantially longer than the pre-set tip portion length 424 or the pre-set base portion length 434. For example, the pre-set body portion length 428 may be 2 to 10 times the pre-set base portion length 434 or the pre-set tip portion length 424. The body portion 414 thus has much greater volume than the tip portion 412 or body portion 416, and will fill much of the volume of an aneurysm into which the device 410 is deployed.

Actual pre-set dimensions of a device may vary depending on the particular application. For treatment of a berry-shaped cerebral aneurysm, a device 410 may have an overall pre-set length 420 of 1 mm to 20 mm, and an overall maximum diameter 422 of 0.5 mm to 10 mm. The pre-set body portion length 428 may be 0.5 mm to 10 mm, with a pre-set body portion maximum diameter 430 of 0.5 mm to 10 mm. The pre-set tip portion length 424 may be 0.1 mm to 5 mm, with a pre-set tip portion maximum diameter 426 of 0.5 mm to 10 mm. The pre-set base portion length 434 may be 0.1 mm to 5 mm, with a pre-set base portion maximum diameter 434 of 0.5 mm to 10 mm. Note that these dimensions are by way of example, and other dimensions are also within the scope of embodiments.

The body portion 414 may have a pre-set body portion diameter 430 which is the same as the pre-set tip portion diameter 426 and/or the pre-set base portion diameter 432. When deployed in an aneurysm, the body portion 414 may assume a larger body portion diameter (i.e., larger than the pre-set diameter) because of the shortening in the body portion length that may be caused by lengthwise pressure on the device from the aneurysm walls.

The device 410 can be radially compressed to a delivery configuration, as depicted in FIG. 4B. When compressed, the device 410 has an overall length 440 and an overall maximum width 442. The overall maximum width 442 when compressed is small enough to enable the device 410 to be positioned within a distal portion of a delivery catheter for advancement to a treatment site, such as using a delivery catheter similar to that depicted and discussed with respect to FIGS. 2A-2B. For example, the device maximum width 442 when compressed to a delivery configuration may be between 0.2 mm to 1.5 mm.

Note that the device overall maximum compressed width 442 (FIG. 4B) is much smaller than the pre-set device overall maximum width 422 (FIG. 4A). For a device 410 that is configured to increase in length responsive to reduction in diameter, such as that depicted, the overall compressed length 440 (FIG. 4B) of the device 410 when compressed is much longer than the pre-set overall length 420 (FIG. 4A).

As will be appreciated, the pre-set configuration (e.g., predetermined and/or superimposed) of an implant 410 according to embodiments may vary depending on the application or to suit the respective purposes for the system, such as the system 200 of FIGS. 2A and 2B. Several variations and configurations of the implant are described in detail below.

As can be appreciated, the specific sizing of a device 410 may be governed by the size of the treatment site or destination vessel and may be easily determined by those skilled in the art. For example, in some embodiments, the device 410 may have a pre-set maximum outer diameter ranging between about 0.5 mm and about 10 mm. In other embodiments, however, the pre-set maximum outer diameter of a device according to embodiments may be less than about 0.5 mm and/or greater than about 10 mm, without departing from the scope of the disclosure.

As discussed above, the material forming the device 410 may exhibit mechanical and/or thermal shape memory characteristics. In some embodiments, the device 410 may be formed of platinum or platinum alloys that have undergone a stress relief anneal process configured to help the device "remember" the superimposed or primary wound shape and automatically expand thereto. In other embodiments, the device 410 may be formed with a nickel-titanium alloy and undergo a heat treatment configured to help the alloy remember a preprogrammed shape. Such a heat treatment may be comprised of restraining the device 410 in the desired shape, heat treating the restrained device 410, then releasing the restraint.

Figure 5A:
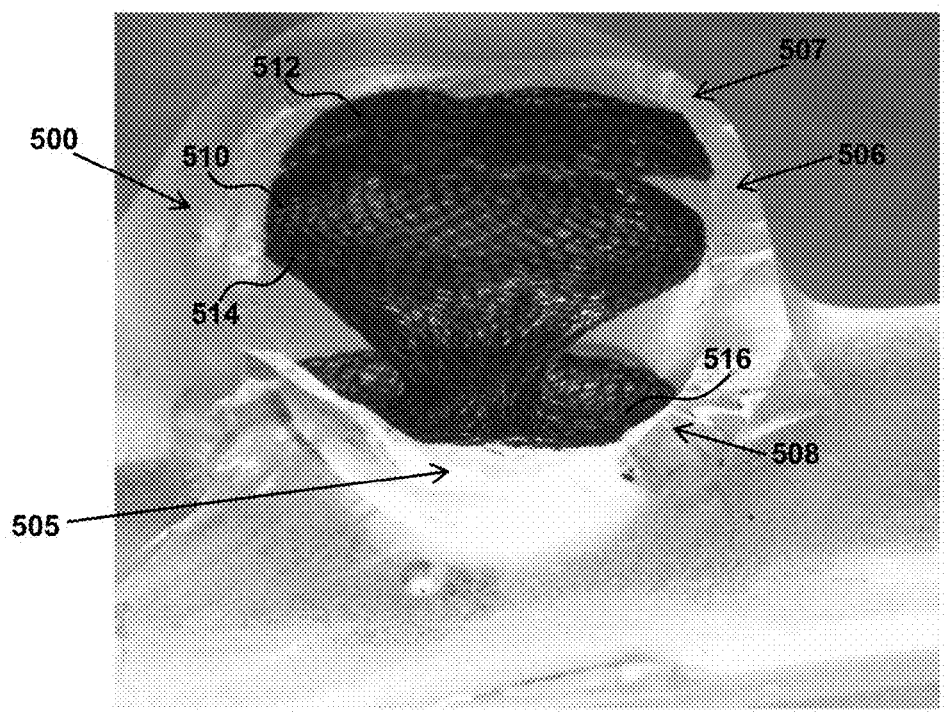
FIG. 5A is a side view of a device deployed in an aneurysm in accordance with some embodiments.

FIG. 5A depicts an aneurysm 500 with device 510 deployed therein in accordance with embodiments. The device 510 is deformed from its pre-set shape (such as that depicted in FIGS. 3D and 4A) to a deployed shape that as depicted largely matches the shape of the aneurysm 500. The tip portion 512 engages against the dome portion 507 of the aneurysm 500, the body portion 514 has expanded to fill most of the volume of the aneurysm 500, and the base portion 516 bridges across the neck 505 and engages against the neck portion of the aneurysm wall 506. The base portion 516 serves to prevent migration of the device 310 out of the aneurysm 500, while also disrupting fluid flow (e.g., blood flow) in and out of the aneurysm. The body portion 514 is compressed lengthwise from its pre-set length, and the tip portion 512 is compressed lengthwise onto the body portion 514 so that the tip portion 512 curves and follows the curvature of the body portion 514.

Figure 5B:
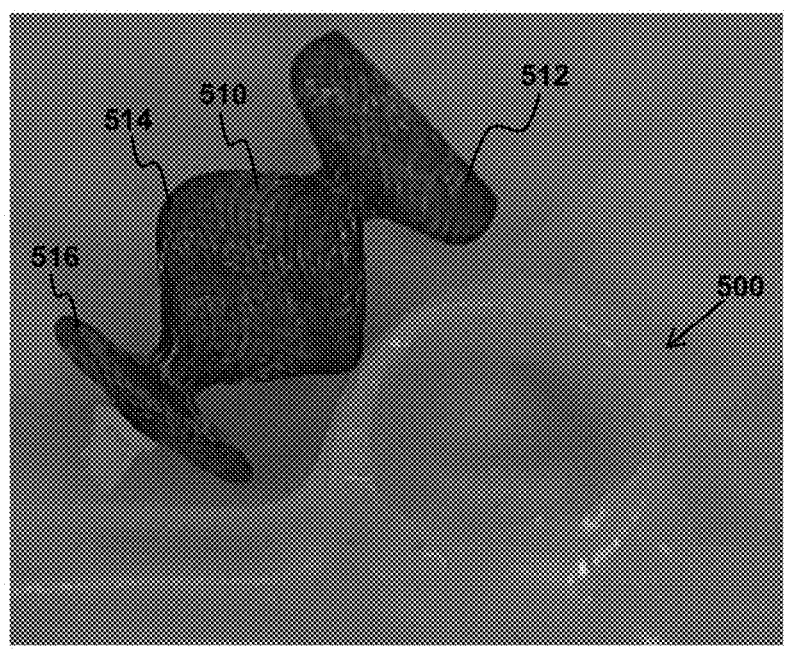
FIG. 5B is a side view of the device of FIG. 5A in a pre-set configuration and adjacent an aneurysm in accordance with some embodiments.

The aneurysm-induced reshaping of the device 510 from its pre-set shape can be seen by comparing the device 510 pre-set shape depicted in FIG. 5B with the aneurysm-constrained device shape in FIG. 5A. FIG. 5B depicts the device 510 expanded to its unconstrained pre-set shape and size, and shown adjacent an aneurysm 500.

For any of the devices disclosed herein, include device 510, the tip portion can comprise a bowl shape while the base portion comprises a disc shape. The concavity of the tip portion can change when the device is deformed in the aneurysm. For example, in an unconstrained, relaxed state outside of the aneurysm, an inner surface of the tip portion can be concave such that the outer surface of the tip portion is convex towards the body portion. As such, the distal end of the tip portion comprises a circumferential ridge (the rim of the bowl). Under compressive forces, however, such as those exerted by the aneurysm wall when the device is implanted within an aneurysm, the tip portion inverts such that the outer surface of the tip portion is concave towards the body portion and the inner surface is now at an outer region of the device (for example as shown in FIG. 5A). Likewise, for any of the embodiments disclosed herein, the base portion can comprise a) a substantially flat disc or b) a bowl facing away from the body portion when the device is in an unconstrained state. Similar to the tip portion, the base portion can deform in response to compressive forces (such as when implanted in an aneurysm) to become concave towards the body portion (as shown, for example, in FIG. 5A).

Figure 6A:
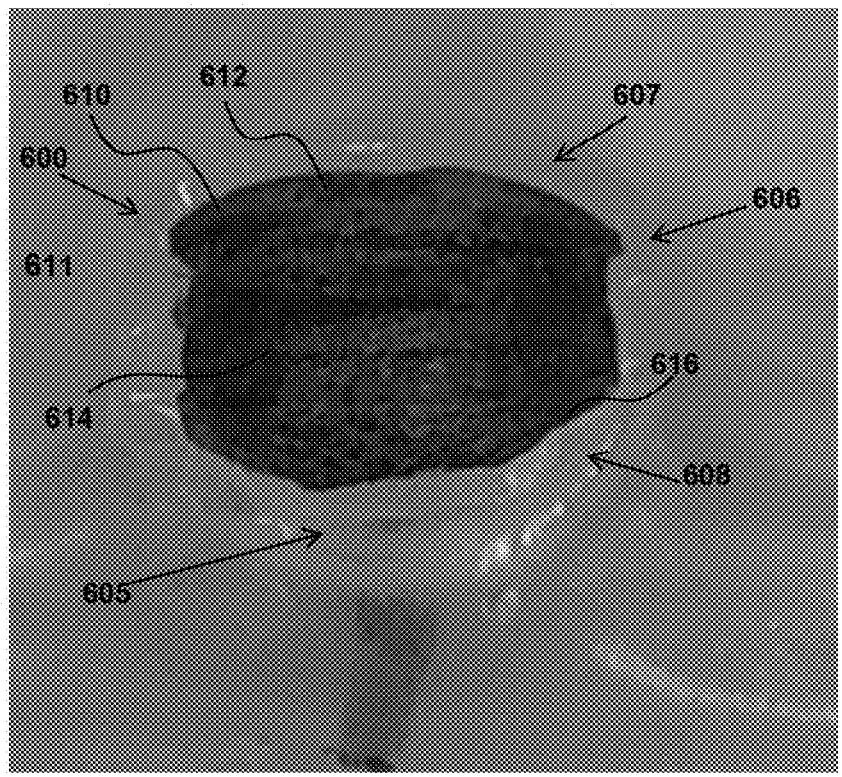
FIG. 6A is a side view of a device deployed in an aneurysm in accordance with some embodiments.

FIG. 6A depicts an aneurysm 600 with device 610 deployed therein in accordance with embodiments. The device 610 is deformed from its pre-set shape (shown in FIG. 6B) to a longitudinally collapsed, deployed shape that as depicted largely matches the shape of the aneurysm 600. When implanted, the tip portion 612 engages against the dome portion 607 of the aneurysm 600, the body portion 614 expands to fill most of the volume of the aneurysm 600, and the base portion 616 extends across the neck 605 and engages the portions of the aneurysm surrounding the neck. The base portion 616 is configured to prevent migration of the device 610 out of the aneurysm 600, while also disrupting fluid flow (e.g., blood flow) in and out of the aneurysm. The body portion 614 is compressed lengthwise from its pre-set length, and the tip portion 612 is compressed lengthwise onto the body 614 so that the tip portion 612 curves and follows the curvature of the body 614. The base portion 614 is also compressed lengthwise from its pre-set length, with the base portion 614 compressed lengthwise onto the body 614 so that the base portion 612 curves and follows the curvature of the body 614. The body portion 614 itself is also compressed along its length.

Figure 6B:
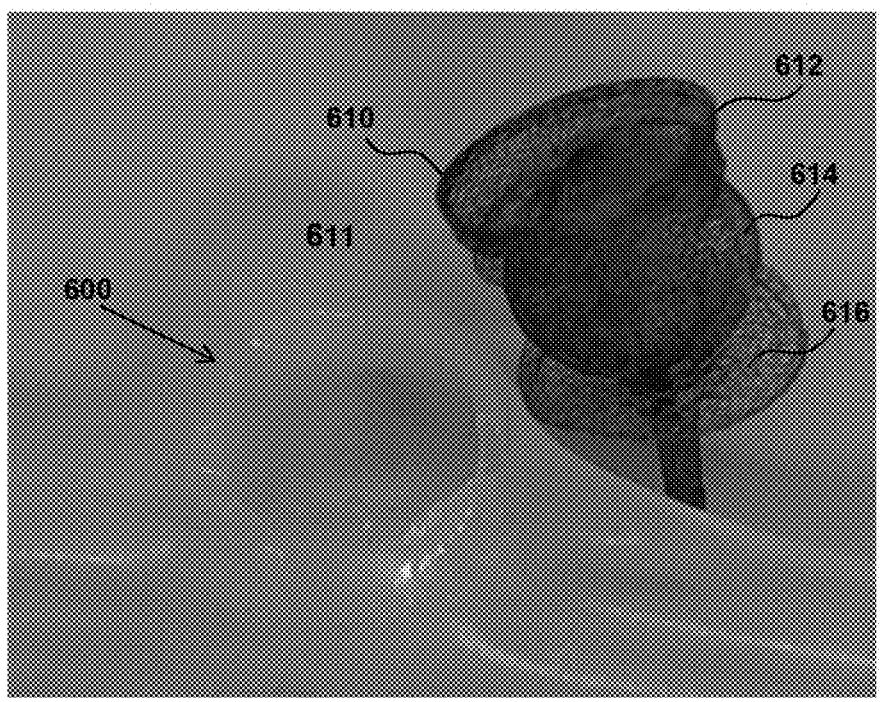
FIG. 6B is a side view of the device of FIG. 6A in a pre-set configuration and adjacent an aneurysm in accordance with some embodiments.

As shown in FIGS. 6A and 6B, in some embodiments the device 600 can include an additional mesh portion 611 between the tip portion 612 and the body portion 614. In an unconstrained and/or deployed configuration, the mesh portion 611 can be concave towards a proximal end of the device 600 (as shown), or can be concave towards a distal end of the device 600. In an unconstrained and/or deployed configuration, the mesh portion 611 can have an opposite direction of concavity to that of the adjacent tip portion 612. For example, as shown in FIG. 6B, in an unconstrained configuration, the mesh portion 611 can have an opposite direction of concavity to the tip portion 612, but in the deployed (implanted) configuration (as shown in FIG. 6A), the mesh portion 611 can have the same direction of concavity as the tip portion 612. In some embodiments, the mesh portion 611 can be positioned between the body portion 614 and the base portion 616. In some embodiments, the device 600 includes a mesh portion between the tip portion 612 and the body portion 614 and a mesh portion between the base portion 616 and the body portion 614.

During deployment, the tip portion 612 can be released to expand first, following by releasing the body portion 614, then releasing the base portion 616. During deployment, the tip portion 612 can be positioned against a dome portion 607 of the aneurysm 600, with the body portion 614 filling most of the volume of the aneurysm 600. The base portion 616 can be positioned so as to extend across the neck 605 of the aneurysm 600, with the base portion 616 engaging against the aneurysm wall in the neck portion 608 areas adjacent to and surrounding the neck 605. The base portion 616 thus prevent migration of the device 610 out of the aneurysm 600 via the neck 605.

The aneurysm-induced reshaping of the device 610 from its pre-set shape can be seen by comparing the device 610 pre-set shape depicted in FIG. 6B with the aneurysm-constrained device shape in FIG. 6A. FIG. 6B depicts the device 610 expanded to its unconstrained pre-set shape and size, and shown adjacent an aneurysm 600. Note that the pre-set shape of the body portion 614 depicted in FIG. 6B is substantially spherical according to embodiments.

Figure 7A:
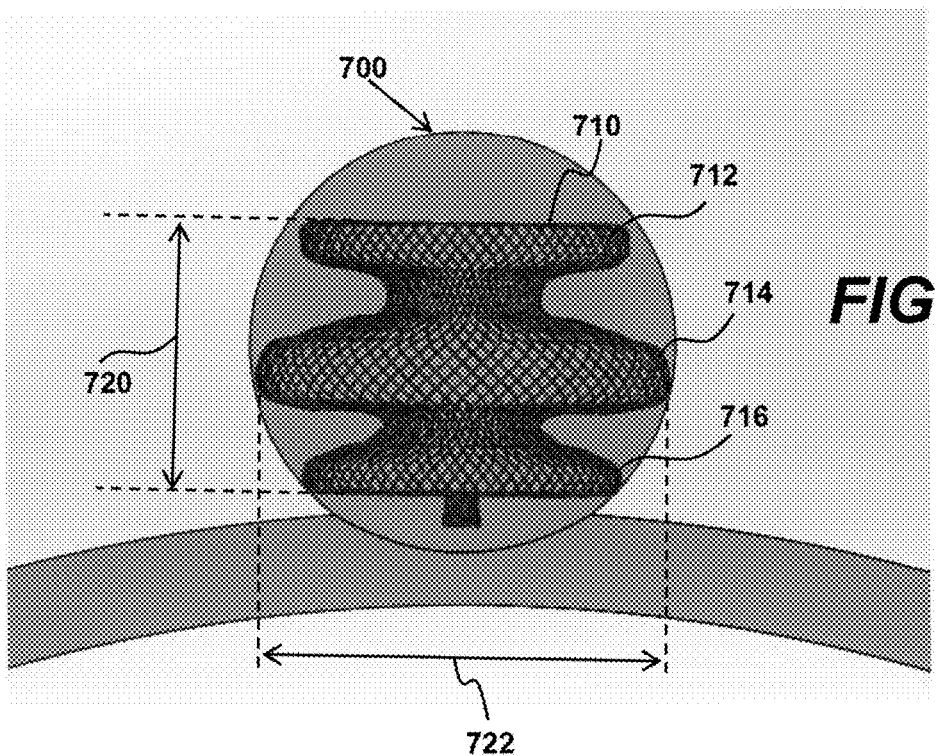
FIG. 7A is a side view of a device deployed in an aneurysm in accordance with some embodiments.
Figure 7B:
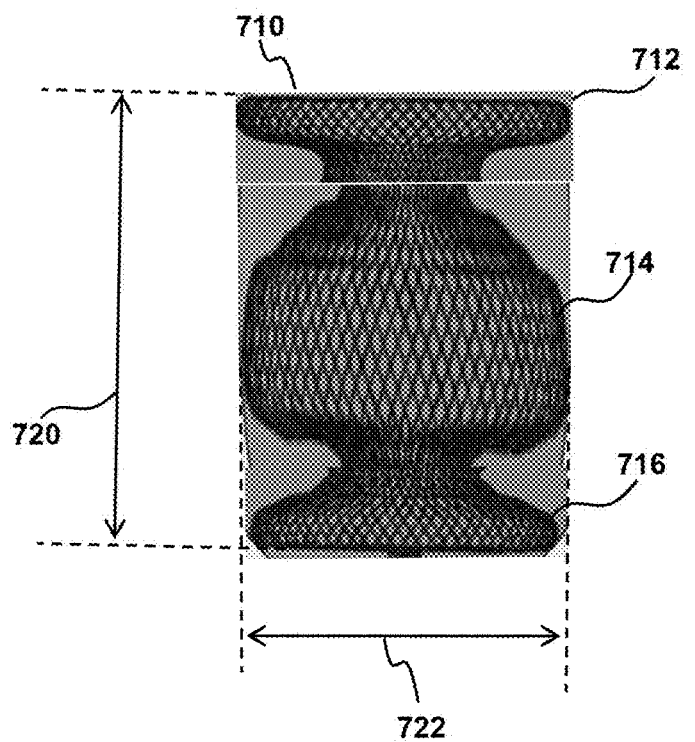
FIG. 7B is a side view of the device of FIG. 7A in a pre-set configuration in accordance with some embodiments.

FIGS. 7A and 7B depict a device 710, with FIG. 7A depicting the device 710 deployed in an aneurysm 700 and FIG. 7B depicting the device 710 in its pre-set shape, in accordance with embodiments. The device 710 deployed in the aneurysm 700 (FIG. 7A) is deformed from its pre-set shape (shown in FIG. 7B) to a deployed/aneurysm-deformed shape that as depicted more closely matches the shape of the aneurysm 700 than does the pre-set shape (FIG. 7B). The body 714 as deployed in the aneurysm is compressed in its length 720 from its pre-set length (FIG. 7B), and also expanded in diameter 722 from its pre-set diameter (FIG. 7B).

Note that throughout this particular application, all device and apparatus dimensions (e.g., widths and lengths of the device) are external dimensions, unless specified otherwise. All dimensions (e.g., widths, diameters, etc.) of patient anatomy (e.g., aneurysms and blood vessels) are internal dimensions (e.g., measured from one interior wall surface to an opposing interior wall surface), unless specified otherwise.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. An aneurysm embolization device, comprising:
 a compressed configuration for intravascular delivery within an elongate shaft to a cerebral aneurysm and an expanded configuration for implantation in the aneurysm, wherein the device is configured to self-expand from the compressed configuration to the expanded configuration;
 a body portion having a first end and a second end, the body portion being self-expandable to a first expanded configuration, wherein the body portion is configured to be positioned in the first expanded configuration such that at least some portions of the body portion engage a wall of the aneurysm;
 an atraumatic tip portion extending from the first end of the body portion and being self-expandable to a second expanded configuration, different in shape or size from the first expanded configuration, wherein the tip portion is configured to be positioned at a dome portion of a wall of the aneurysm in the second expanded configuration to engage the dome portion; and
 a base portion extending from the second end of the body portion and being self-expandable to a third expanded configuration, different in shape or size from the first expanded configuration, and wherein the base portion comprises a neck-engaging surface, wherein the base portion is configured to be positioned at a neck of an intracranial aneurysm in the third expanded configuration such that base portion extends across the neck and the neck-engaging surface engages against a neck portion of the aneurysm wall surrounding the neck.

2. The device of claim 1, wherein the body portion, the tip portion, and the base portion comprise a single unitary structure.

3. The device of claim 1, wherein the body portion, the tip portion, and the base portion comprise at least one continuous braid.

4. The device of claim 1, wherein the device is configured to be placed in an aneurysm such that the tip portion is interposed between the body portion and the dome of the aneurysm wall, and such that the base portion is interposed between the body portion and the neck of the aneurysm.

5. The device of claim 1, wherein a pre-set length of the body portion is different from a pre-set length of the base portion.

6. The device of claim 1, wherein a pre-set length of the body portion is greater than a pre-set length of the base portion.

7. The device of claim 1, wherein a pre-set length of the body portion is at least twice as long as a pre-set base length of the base portion.

8. The device of claim 1, wherein a pre-set length of the body portion is different than a pre-set length of the tip portion.

9. The device of claim 1, wherein a pre-set length of the body portion is greater than a pre-set length of the tip portion.

10. The device of claim 1, wherein a pre-set length of the body portion is at least twice as long as a pre-set base length of the tip portion.

11. The device claim 1, wherein a pre-set maximum diameter of the body portion is between 90% and 110% of a pre-set maximum diameter of the base portion.

12. The device of claim 1, wherein a pre-set maximum diameter of the body portion is between 90% and 110% of a pre-set maximum diameter of the tip portion.

13. The device of claim 1, wherein the device further comprises a lumen extending continuously though the base portion, the body portion, and the tip portion.

14. The device of claim 1, wherein:
 the tip portion connects to the body portion at a distal waist, and wherein the base portion connects to the body portion at a proximal waist; and
 in the pre-set configuration the distal waist is narrower than the body portion and the tip portion, and the proximal waist is narrower than the body portion and the base portion.

15. The device of claim 1, wherein the tip portion has an inner surface and an outer surface, and wherein, at least when the device is in an unconstrained state outside of the aneurysm, an inner surface of the tip portion can be concave such that an outer surface of the tip portion is convex towards the body portion.

16. The device of claim 15, wherein, at least when the device is in the unconstrained state outside of the aneurysm, the base portion comprises a disc shape.

17. The device of claim 16, wherein, at least when the device is in the unconstrained state outside of the aneurysm, the body portion comprises a disc shape.

* * * * *